United States Patent
Shorr

(10) Patent No.: US 11,337,960 B2
(45) Date of Patent: May 24, 2022

(54) METHODS AND COMPOSITIONS FOR THE TREATMENT OF PRE-DIABETES, DIABETES AND METABOLIC SYNDROME

(71) Applicant: Pre-D Partners LLC, Highland Park, NJ (US)

(72) Inventor: Robert Shorr, Edison, NJ (US)

(73) Assignee: Pre-D Partners LLC, Highland Park, NJ (US)

( * ) Notice: Subject to any disclaimer, the term of this patent is extended or adjusted under 35 U.S.C. 154(b) by 116 days.

(21) Appl. No.: 15/521,216

(22) PCT Filed: Oct. 26, 2015

(86) PCT No.: PCT/US2015/057382
§ 371 (c)(1),
(2) Date: Apr. 21, 2017

(87) PCT Pub. No.: WO2016/065360
PCT Pub. Date: Apr. 28, 2016

(65) Prior Publication Data
US 2017/0354640 A1 Dec. 14, 2017

Related U.S. Application Data

(60) Provisional application No. 62/068,028, filed on Oct. 24, 2014.

(51) Int. Cl.
*A61K 31/385* (2006.01)
*A61K 45/06* (2006.01)
*A61K 38/16* (2006.01)
*A61K 31/593* (2006.01)
*A61K 31/592* (2006.01)
*C07K 14/47* (2006.01)

(52) U.S. Cl.
CPC .......... *A61K 31/385* (2013.01); *A61K 31/592* (2013.01); *A61K 31/593* (2013.01); *A61K 45/06* (2013.01); *C07K 14/4703* (2013.01); *A01K 2267/0362* (2013.01); *A61K 38/16* (2013.01); *A61K 2300/00* (2013.01)

(58) Field of Classification Search
CPC .... A61K 31/385; A61K 47/18; A61K 47/186; A61K 31/205; A61K 31/122; A61K 47/183; A61K 31/155; A61K 8/43; A01K 2267/0362
See application file for complete search history.

(56) References Cited

U.S. PATENT DOCUMENTS

| 6,048,846 | A | * | 4/2000 | Cochran | A61K 45/06 424/423 |
| 6,365,622 | B1 | | 4/2002 | Cavazza | |
| 6,368,617 | B1 | * | 4/2002 | Hastings | A61K 31/565 424/439 |
| 2004/0034030 | A1 | * | 2/2004 | Richardson | A61K 31/198 514/251 |
| 2006/0216251 | A1 | * | 9/2006 | Morariu | A61K 8/41 424/59 |
| 2008/0317725 | A1 | * | 12/2008 | Baum | A61K 31/05 424/94.1 |
| 2010/0021573 | A1 | * | 1/2010 | Gonzalez | A61K 31/122 424/766 |
| 2010/0041622 | A1 | * | 2/2010 | Bromley | A61K 9/107 514/52 |
| 2010/0209497 | A1 | * | 8/2010 | Thornthwaite | A61K 31/122 424/456 |
| 2011/0129442 | A1 | | 6/2011 | Magri' et al. | |
| 2011/0287109 | A1 | * | 11/2011 | Bagley | A61K 31/07 424/638 |
| 2013/0251696 | A1 | | 9/2013 | Cornelli | |
| 2014/0017222 | A1 | * | 1/2014 | Gonzalez | A61K 31/122 424/94.4 |

FOREIGN PATENT DOCUMENTS

| FR | 2964834 A1 * | 3/2012 | A61K 31/315 |
| FR | 2964834 A1 * | 3/2012 | A61K 31/315 |
| WO | WO2011005310 A1 * | 1/2011 | A61K 36/185 |

OTHER PUBLICATIONS

Dasgupta, A. (Antioxidants n Food, Vitamins and Supplements, 2004, p. 26, line 5, obtained from www.sciencedirect.com). (Year: 2004).*
GeroNova Research Inc. (Different Forms of Lipoic Acid, obtained online via www.geronova.com.) (Year: 2018).*
Article: Concept 5 Review ( L- and D-Amino Acids), obtained online via www.phschool.com. (Year: 2020).*
Definition of ubiquinone—NCI Dictionary of Cancer Terms—National Cancer Institute, via www.cancer.gov. (Year: 2021).*
International Search Report, dated Feb. 5, 2016, for International Application No. PCT/2015/057382.
Written Opinion of the International Searching Authority, dated Feb. 5, 2016, for International Application No. PCT/2015/057382.
Lukaszuk et al. "Effects of R-Alpha Lipoic Acid on HbA1c, Lipids and Blood Pressure in Type-2 Diabetics: A Preliminary Study." Journal of Complementary and Integrative Medicine, vol. 6 (2009), Iss. 1, Art. 32.

* cited by examiner

*Primary Examiner* — Sue X Liu
*Assistant Examiner* — Mei Ping Chui
(74) *Attorney, Agent, or Firm* — Morgan Lewis & Bockius LLP

(57) ABSTRACT

The disclosure provides thiol-containing alkyl fatty acid compound formulations for intravenous, parenteral or oral administration. The compositions of the present technology have optimal controlled bioavailability and are useful for treating metabolic dysfunctions such as pre-diabetes, Metabolic Syndrome and diabetes. Also provided are methods of treatment comprising the daily administration of the disclosed thiol-containing alkyl fatty acid formulations.

4 Claims, 2 Drawing Sheets

METHODS AND COMPOSITIONS FOR THE TREATMENT OF PRE-DIABETES,
DIABETES AND METABOLIC SYNDROME

| HbA1c | AVG. BLOOD GLUCOSE |
|---|---|
| % | mg/dl |
| 6 | 126 |
| 6.5 | 140 |
| 7 | 154 |
| 7.5 | 169 |
| 8 | 183 |
| 8.5 | 197 |
| 9 | 212 |
| 9.5 | 226 |
| 10 | 240 |

FIG. 1B

METHODS AND COMPOSITIONS FOR THE TREATMENT OF PRE-DIABETES, DIABETES AND METABOLIC SYNDROME

CROSS-REFERENCE TO RELATED APPLICATIONS

The present application is a national stage application, filed under 35 U.S.C. 071, of PCT Application No. PCT/US2015/057382, filed Oct. 26, 2015, which claims the benefit of priority to U.S. Application No. 62/068,028, filed Oct. 24, 2014, the content of which is incorporated herein by reference in its entirety.

TECHNICAL FIELD

The present disclosure relates generally to compositions comprising a combination of synthetic chemical agents and herbal extracts as nutritional and dietary supplements and their methods of use for the treatment of metabolic dysfunction.

BACKGROUND

Much attention has been paid to the concept of "we are what we eat." While at a superficial level this would be reasonable, mammals are in fact much more dependent on what they can (i) digest in the gut, (ii) absorb into the blood stream, (iii) deliver to organs, tissues, cells and organelles in a form that it useful in meeting metabolic needs. Both catabolic and anabolic processes are required to support healthy function. The transport of nutrients into cells and their distribution into the appropriate organelles for metabolism is highly regulated but yet is responsive to dietary changes. Mitochondria play a central role in the production of ATP, the formation of biosynthetic intermediates as well as the production of signal transduction molecules involved in growth and differentiation and homeostasis. Changes in these processes as a result of genetics, exposure to pathogens or dietary extremes can stress the body to the point of disease manifestation. Excessive consumption of processed foods, sugar and inappropriate types and levels of fats may contribute to a variety of ailments including, but not limited to, diabetes, cardiovascular disease, gout, and inflammatory disease.

Nutritional supplements can play an important role in reversing or preventing these diseases. In many instances, the bioavailability of one nutrient is required along with others for the optimal treatment and maintenance of health. In an age of highly processed foods, key nutrients such as vitamins and essential enzyme cofactors, may be lacking or may be destroyed during preparation. However, mere replacement of these missing nutrients by consuming tablets, powders or capsules containing one or more of these nutrients is insufficient because metabolism is a concert of activities and each nutrient, cofactor and enzyme has specific temporal, spatial and structural requirements in the context of these orchestrated metabolic events. It is thus not only a question of what we eat, digest and can absorb in a usable form, i.e. the collective "what" but also "when and where."

Insulin receptors are desensitized and the ability to clear glucose from the blood is compromised in patients with Metabolic Syndrome, pre-diabetes, or diabetes. Given the severe health risks associated with pre-diabetes, diabetes and Metabolic Syndrome, there is a need for safe and effective therapeutics.

SUMMARY

The present disclosure provides alkyl fatty acid formulations and vitamin D compound formulations, selected on the basis of non-anticipated synergies and wherein at least two, at least three, or at least four or more of the individual components of the thiol-containing alkyl fatty acid formulations and vitamin D compound formulations of the present technology have overlapping oral bioavailability. The formulations of the present technology permit cells to have a contemporaneous degree of exposure to the components of the formulations disclosed herein that is otherwise cost prohibitive or impractical by the dosing of individual components independently. For example, depending on the dosage and the form of the medicament (e.g., a capsule, tablet, or powder) the requisite numbers of units of each component to be ingested may be difficult. Each preparation of an individual ingredient will have its own dissolution kinetics, thus affecting the level of bioavailability and plasma pharmacokinetics. An additional concern is that the levels of fillers or excipients multiplied by the numbers of capsules or tablets can contribute to toxicities within patients.

In one aspect, the present disclosure provides a thiol-containing alkyl fatty acid formulation comprising a thiol-containing alkyl fatty acid, a N-acetyl-L-carnitine derivative, an antioxidant, and at least one amino acid, wherein the thiol-containing alkyl fatty acid is lipoic acid or alpha-lipoic acid.

In some embodiments, the thiol-containing alkyl fatty acid is a mixture of R and S isomers of alpha-lipoic acid. Additionally or alternatively, in some embodiments of the thiol-containing alkyl fatty acid formulation, the N-acetyl-L-carnitine derivative is L-carnitine. Additionally or alternatively, in certain embodiments of the thiol-containing alkyl fatty acid formulation, the antioxidant is selected from the group consisting of CoQ10, quercetin, and other plant-derived flavonoids. Additionally or alternatively, in some embodiments of the thiol-containing alkyl fatty acid formulation, the at least one amino acid is one or more of the amino acids selected from the group consisting of propionyl L-carnitine, L-tartarate, L-glutamine, L-theanine and L-arginine.

In some embodiments of the thiol-containing alkyl fatty acid formulation, the thiol-containing alkyl fatty acid is alpha-lipoic acid, the N-acetyl-L-carnitine derivative is L-carnitine, the antioxidant is CoQ10 and the amino acids are L-glutamine and L-arginine. In some embodiments, the ratio of alpha-lipoic acid to L-carnitine is 1.5:1. Additionally or alternatively, in some embodiments, the ratio of alpha-lipoic acid to CoQ10 is 6:1. Additionally or alternatively, in certain embodiments, the ratio of alpha-lipoic acid to L-glutamine is 1:1.25. Additionally or alternatively, in some embodiments, the ratio of alpha-lipoic acid to L-arginine is 1:2.5.

In any of the above embodiments, the thiol-containing alkyl fatty acid formulation further comprises one or more of melatonin, proteins, peptides, protease inhibitors, trace elements, botanical extracts, and carbohydrates. In some embodiments of the thiol-containing alkyl fatty acid formulation, the protein is serratiopeptidase. Additionally or alternatively, in some embodiments of the thiol-containing alkyl fatty acid formulation, the trace element is indium sulfate. Additionally or alternatively, in some embodiments of the thiol-containing alkyl fatty acid formulation, the protease inhibitor is soybean trypsin inhibitor, leupeptin, or pepstatin. Additionally or alternatively, in some embodiments of the thiol-containing alkyl fatty acid formulation, the botanical extracts are one or more plant extracts selected from the group consisting of eggplant extract, resveratrol-containing extracts such as grape and grape seed extracts, guaraná extract, purified or synthetic whole-plant cannabis extract, vanilla extract, cinnamon, nutmeg, cloves, and turmeric. Additionally or alternatively, in some embodiments of the thiol-containing alkyl fatty acid formulation, the carbohydrate is selected from the group consisting of beta-glucans, fiber extracts, fruit pulps, simple and complex sugars. In some embodiments, the beta-glucan is β-1,3-glucan or β-1, 6-glucan. Additionally or alternatively, in some embodiments of the thiol-containing alkyl fatty acid formulation, the formulation comprises 600 mg alpha-lipoic acid, 400 mg L-carnitine, 100 mg CoQ10, 750 mg L-glutamine and 1500 mg L-arginine.

In another aspect, the present disclosure provides a vitamin D compound formulation comprising a vitamin D compound, a sulfur donor and one or more sedatives or sleep promoting agents, wherein the vitamin D compound is cholecalciferol (D3) or ergocalciferol (D2). In some embodiments of the vitamin D compound formulation, the sulfur donor is methylsulfonylmethane. Additionally or alternatively, in some embodiments of the vitamin D compound formulation, the one or more sedatives or sleep promoting agents are selected from the group consisting of melatonin, L-theanine, chamomile extract, valerian extract, 5-hydroxytryptamine (5-HT), 5HTP (L-5-hydroxytryptophan), D-phenylalanine, L-phenylalanine, or a mixture of D- and L-phenylalanine.

In any of the above embodiments, the vitamin D compound formulation further comprises melatonin, proteins, peptides, protease inhibitors, trace elements, botanical extracts, and carbohydrates. In some embodiments of the vitamin D compound formulation, the protein is serratiopeptidase. Additionally or alternatively, in some embodiments of the vitamin D compound formulation, the trace element is indium sulfate. Additionally or alternatively, in some embodiments of the vitamin D compound formulation, the protease inhibitor is soybean trypsin inhibitor, leupeptin, or pepstatin. Additionally or alternatively, in some embodiments of the vitamin D compound formulation, the botanical extracts are one or more plant extracts selected from the group consisting of eggplant extract, resveratrol-containing extracts such as grape and grape seed extracts, guaraná extract, purified or synthetic whole-plant cannabis extract, vanilla extract, cinnamon, nutmeg, cloves, and turmeric. Additionally or alternatively, in some embodiments of the vitamin D compound formulation, the carbohydrate is selected from the group consisting of beta-glucans, fiber extracts, pulps, simple and complex sugars. In some embodiments, the beta-glucan is β-1,3-glucan or β-1,6-glucan. Additionally or alternatively, in some embodiments of the vitamin D compound formulation, the formulation comprises 1000 IU vitamin D, 400 mg L-theanine, 400 mg methylsulfonylmethane, 50 mg 5-HTP, 3 mg melatonin, 600 mg valerian root powder, and 500 mg chamomile powder.

Additionally or alternatively, any of the formulations disclosed herein may be provided as an oral solid medicament in the form of tablets, capsules, nanoparticles, or nano-emulsions for immediate or sustained release. The formulations of the present technology may comprise a plurality of crystalline structures. The formulations can also contain additional ingredients or encapsulations that establish the release profile of each or the collective ingredient(s) for instantaneous release, or sustained release. In a further embodiment, the oral solid dosage form can be enterically coated so as to prevent gastric irritation in the subject. Alternatively, the formulations of the present technology can be either fully dissolved or prepared as an emulsion.

In one aspect, the present disclosure provides methods for treating or preventing pre-diabetes, diabetes or Metabolic Syndrome, and/or treating or preventing the signs or symptoms of pre-diabetes, diabetes or Metabolic Syndrome in a subject in need thereof comprising administering to the subject a therapeutically effective amount of at least one of the formulations disclosed herein, thereby resulting in the prevention or treatment of one or more signs or symptoms of pre-diabetes, diabetes or Metabolic Syndrome. In some embodiments of the method, the subject exhibits a reduction in Body Mass Index (BMI) after administration of at least one of the formulations disclosed herein. In some embodiments of the method, the subject exhibits a reduction in glycated hemoglobin levels (HbA1c) after administration of at least one of the formulations disclosed herein. In some embodiments of the method, the weight status of the subject shifts from overweight to normal weight after administration of at least one of the formulations disclosed herein.

In some embodiments of the method, the signs or symptoms of pre-diabetes, diabetes or Metabolic Syndrome include one or more of body weight, fasting glucose/insulin/free fatty acid, glucose tolerance (OGTT), muscle insulin sensitivity, markers of insulin signaling (e.g., Akt-P, IRS-P), serum triglyceride levels, HDL and LDL cholesterol levels, blood pressure, serum fibrinogen or plasminogen activator inhibitor levels, levels of C-reactive protein, insulin resistance, glucose intolerance, elevated levels of glycosylated blood proteins (e.g., hemoglobin).

In another aspect, the present disclosure provides methods for treating a disease or condition characterized by elevated glycated hemoglobin levels (HbA1c) in a subject in need thereof comprising administering to the subject a therapeutically effective amount of at least one of the formulations disclosed herein. In some embodiments of the method, the disease or condition characterized by elevated glycated hemoglobin levels (HbA1c) is selected from the group consisting of pre-diabetes, diabetes, Metabolic Syndrome, insulin resistance, glucose intolerance or cardiovascular disease, and stroke. In some embodiments, the fasting plasma glucose level (FPG) of the subject prior to administration of at least one of the formulations disclosed herein is at least 5.6 mmol/L. In some embodiments of the method, the subject exhibits a reduction in glycated hemoglobin levels (HbA1c) after administration of at least one of the formulations disclosed herein.

In some embodiments of the methods of the present technology, the subject is human.

Additionally or alternatively, in some embodiments of the methods of the present technology, the formulations of the present technology are administered orally, topically, intranasally, systemically, intravenously, subcutaneously, intraperitoneally, intradermally, intraocularly, iontophoretically, transmucosally, or intramuscularly.

In some embodiments of the methods of the present technology, at least one of the formulations of the present technology is administered daily for 1 week or more. In some embodiments of the methods of the present technology, at least one of the formulations of the present technology is administered daily for 2 weeks or more. In some embodiments of the methods of the present technology, at least one of the formulations of the present technology is administered daily for 3 weeks or more. In some embodiments of the methods of the present technology, at least one of the formulations of the present technology is administered daily for 4 weeks or more. In some embodiments of the methods of the present technology, at least one of the formulations of the present technology is administered daily for 6 weeks or more. In some embodiments of the methods of the present technology, at least one of the formulations of the present technology is administered daily for 12 weeks or more.

BRIEF DESCRIPTION OF THE DRAWINGS

FIGS. 1A and 1B shows the standard curve and correlation between HbA1c levels (%) and estimated average blood glucose (mg/dL). The relationship between HbA1c and estimated average blood glucose (eAG) is described by the formula 28.7×HbA1c−46.7=eAG. FIG. 1 is adapted from the American Diabetes Association website and is available at professional.diabetes.org/glucosecalculator.aspx.

DETAILED DESCRIPTION

Figure 1A:
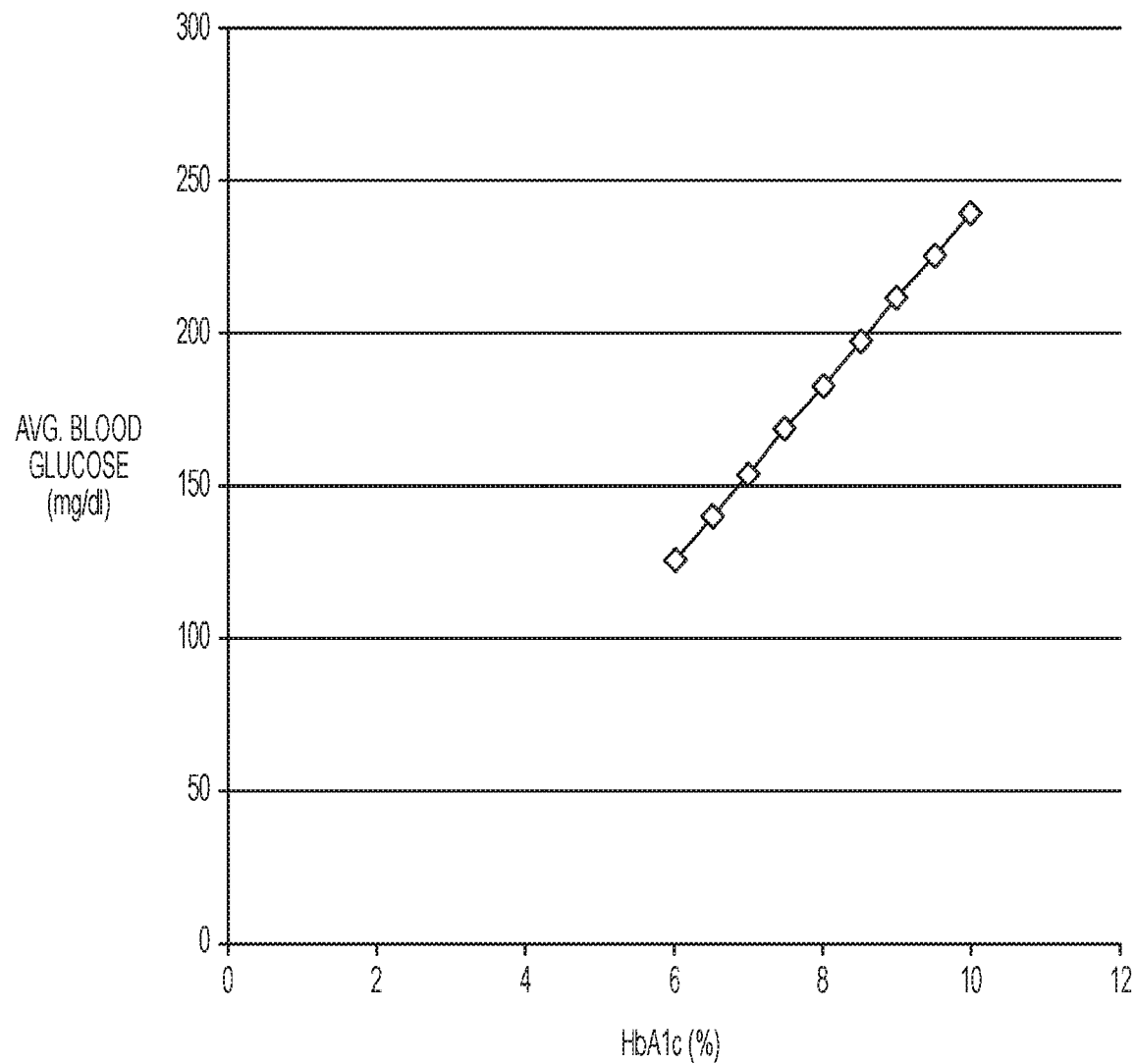

It is to be appreciated that certain aspects, modes, embodiments, variations and features of the present technology are described below in various levels of detail in order to provide a substantial understanding of the present technology. The definitions of certain terms as used in this specification are provided below. Unless defined otherwise, all technical and scientific terms used herein generally have the same meaning as commonly understood by one of ordinary skill in the art to which this present technology belongs.

As used in this specification and the appended claims, the singular forms "a", "an" and "the" include plural referents unless the content clearly dictates otherwise. For example, reference to "a cell" includes a combination of two or more cells, and the like.

All numerical designations, e.g., pH, temperature, time, concentration and molecular weight, including ranges, are approximations which are varied (+) or (−) by increments of 1.0 or 0.1, as appropriate, or alternatively by a variation of +/−10%, or alternatively 5% or alternatively 2%. It is to be understood, although not always explicitly stated, that all numerical designations are preceded by the term "about".

As used herein, the "administration" of an agent, drug, or formulation to a subject includes any route of introducing or delivering to a subject a compound to perform its intended function. Administration can be carried out by any suitable route, including orally, intranasally, parenterally (intravenously, intramuscularly, intraperitoneally, or subcutaneously), systemically, intradermally, intraocularly, iontophoretically, transmucosally, intramuscularly, or topically. Administration includes self-administration and the administration by another.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid Amino acids can be referred to herein by either their commonly known three letter symbols or by the one-letter symbols recommended by the IUPAC-IUB Biochemical Nomenclature Commission.

As used herein, the term "effective amount" refers to a quantity sufficient to achieve a desired therapeutic and/or prophylactic effect, e.g., an amount which results in the reduction of insulin resistance, reduction of glucose intolerance and reduction of levels of glycosylated blood proteins such as hemoglobin, or which results in partial or full amelioration of one or more symptoms of diabetes, pre-diabetes and Metabolic Syndrome. In the context of therapeutic or prophylactic applications, in some embodiments, the amount of a formulation administered to the subject will depend on the type, degree, and severity of the disease and on the characteristics of the individual, such as general health, age, sex, body weight and tolerance to drugs. The skilled artisan will be able to determine appropriate dosages depending on these and other factors. In the methods described herein, the compositions of the present technology may be administered to a subject having one or more signs, symptoms, or risk factors of diabetes, pre-diabetes and Metabolic Syndrome, including, but not limited to, e.g., body weight, fasting glucose/insulin/free fatty acid, glucose tolerance (OGTT), muscle insulin sensitivity, markers of insulin signaling (e.g., Akt-P, IRS-P), serum triglyceride levels, HDL and LDL cholesterol levels, blood pressure, serum fibrinogen or plasminogen activator inhibitor levels, levels of C-reactive protein, insulin resistance, glucose intolerance, elevated levels of glycosylated blood proteins (e.g., hemoglobin) etc. For example, a "therapeutically effective amount" of the formulations includes levels at which the presence, frequency, or severity of one or more signs, symptoms, or risk factors of diabetes, pre-diabetes and Metabolic Syndrome are reduced or eliminated. In some embodiments, a therapeutically effective amount reduces or ameliorates the physiological effects of diabetes, pre-diabetes and Metabolic Syndrome, and/or the risk factors of diabetes, pre-diabetes and Metabolic Syndrome, and/or the likelihood of developing diabetes, pre-diabetes and Metabolic Syndrome.

As used herein, the terms "polypeptide," "peptide," and "protein" are used interchangeably herein to mean a polymer comprising two or more amino acids joined to each other by peptide bonds. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, the terms "subject," "individual," or "patient" can be an individual organism, a vertebrate, a mammal, or a human.

A "synergistic therapeutic effect" refers to a greater-than-additive therapeutic effect which is produced by a combination of at least two therapeutic agents, and which exceeds that which would otherwise result from the individual administration of the agents. For example, lower doses of one or more therapeutic agents may be used in treating pre-diabetes, diabetes or Metabolic Syndrome, resulting in increased therapeutic efficacy and decreased side-effects.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder.

As used herein, "prevention" or "preventing" of a disorder or condition refers to a compound that, in a statistical sample, reduces the occurrence of the disorder or condition in the treated sample relative to an untreated control sample, or delays the onset of one or more symptoms of the disorder or condition relative to the untreated control sample. As used herein, preventing pre-diabetes, diabetes or Metabolic Syndrome includes preventing or delaying the initiation of pre-diabetes, diabetes or Metabolic Syndrome. As used herein, prevention of pre-diabetes, diabetes or Metabolic Syndrome also includes preventing a recurrence of one or more signs or symptoms of pre-diabetes, diabetes or Metabolic Syndrome.

It is also to be appreciated that the various modes of treatment or prevention of medical conditions as described herein are intended to mean "substantial," which includes total but also less than total treatment or prevention, and wherein some biologically or medically relevant result is achieved.

All metabolic processes either produce or require energy. In mammals, "energy" is derived from glucose, fats and other fuel sources and is converted to and transported as ATP. Energy production involves a coordination of cellular events at the macro and micro levels. The cellular machinery necessary for processing fuel into energy and synthetic intermediates must be present and in good working order. Fuels must be transported to where they need to go and in a form suitable for processing. The right substrates must contact the proper cellular machinery at the right time and place, and the movement of substrates and byproducts in and out of cells and organs must be regulated.

All biological activities are dependent on the availability of ATP. While ATP can be produced in the cell cytosol, the primary point of production is within the mitochondria. The absence of nutrients required for mitochondrial function, or the presence of cellular deformation or deregulation can lead to pathology.

It is desirable to have medicaments in a novel combination with lipoic acid wherein the combination demonstrates synergistic effects in both mechanism of action and clinical efficacy.

In some embodiments, the present disclosure provides thiol-containing alkyl fatty acid formulations that improve glucose uptake and the oxidation of nutrients, either alone or in combination with a vitamin D compound formulation. In some embodiments, the thiol-containing alkyl fatty acid formulations of the present technology, alone or in combination with the vitamin D compound formulations of the present technology are useful in treating or preventing insulin resistance in a subject (including, but not limited to, a subject diagnosed with pre-diabetes, diabetes or Metabolic Syndrome).

The present disclosure provides compositions and methods for treating pre-diabetes, diabetes, Metabolic Syndrome, insulin resistance, glucose intolerance and elevated glycated hemoglobin levels (HbA1c) in a subject in need thereof. The formulations of the present technology permit cells to have a contemporaneous degree of exposure to the components of the formulations disclosed herein that is otherwise cost prohibitive or impractical by the dosing of individual components independently. For example, depending on the dosage and the form of the medicament (e.g., a capsule, tablet, or powder) the requisite numbers of units of each component to be ingested may be difficult. Each preparation of an individual ingredient will have its own dissolution kinetics, thus affecting the level of bioavailability and plasma pharmacokinetics. An additional concern is that the levels of fillers or excipients multiplied by the numbers of capsules or tablets can contribute to toxicities within patients.

Pre-Diabetes, Diabetes and Metabolic Syndrome

The diabetic, Metabolic Syndrome and the pre-diabetic states have often been characterized with respect to insulin, e.g., an insufficient amount of insulin, ineffective insulin, insulin resistance and insulin desensitization. Normal glucose tolerance in healthy control subjects is defined as a Fasting Plasma Glucose level (FPG) of <5.6 mmol/L and a 2 hour plasma glucose level (PG) of <7.8 mmol/L in response to a 75 g oral glucose tolerance test (OGTT). Nathan et al., Impaired Fasting Glucose and Impaired Glucose Tolerance: Implications for Care. A Consensus Statement from the American Diabetes Association. *Diabetes Care* 30:753-9 (2007). Diabetes is defined as a FPG≥7.0 mmol/L or a 2 hour PG≥11.1 mmol/L during an OGTT. Pre-diabetes is an intermediate state of altered glucose metabolism with a heightened risk of developing type 2 diabetes and other associated complications. There are two categories of pre-diabetes: (a) impaired fasting glucose (IFG), defined by a FPG≥5.6 mmol/L but <7.0 mmol/L and (b) impaired glucose tolerance (IGT), defined by a FPG <7.0 mmol/L with a 2 h PG during an OGTT ≥7.8 mmol/L and <11.1 mmol/L. IFG and IGT can occur as mutually exclusive conditions (isolated IFG or isolated IGT) or they can occur in combination (combined IFG and IGT). Nathan et al., Impaired Fasting Glucose and Impaired Glucose Tolerance: Implications for Care. A Consensus Statement from the American Diabetes Association. *Diabetes Care* 30:753-9 (2007).

Metabolic Syndrome, also known as syndrome X and dysmetabolic syndrome, is a collection of health disorders or risks that increase the chance of developing heart disease, stroke, and diabetes. Metabolic Syndrome may include a variety of underlying metabolic phenotypes, including insulin resistance and/or obesity predisposition phenotypes. Metabolic Syndrome is often characterized by any of a number of metabolic disorders or risk factors, which are generally considered to most typify Metabolic Syndrome when more than one of these factors are present in a single individual. The factors include: central obesity (disproportionate fat tissue in and around the abdomen), atherogenic dyslipidemia (which includes a family of blood fat disorders including, e.g., high triglycerides, low HDL cholesterol, and high LDL cholesterol that can foster plaque buildups in the vascular system, including artery walls), high blood pressure, insulin resistance or glucose intolerance (the inability to properly use insulin or blood sugar), a chronic prothrombotic state (e.g., characterized by high fibrinogen or plasminogen activator inhibitor levels in the blood), and a chronic proinflammatory state (e.g., characterized by higher than normal levels of high-sensitivity C-reactive protein in the blood). People with Metabolic Syndrome are at increased risk of coronary heart disease, other diseases related to plaque buildups in artery walls (e.g., stroke and peripheral vascular disease) and type 2 diabetes. The underlying causes of metabolic syndrome are unclear. Genetics, diet, disrupted chronobiology, mood disorders and alcohol use or exposure to pollutants e.g., tobacco may be implicated in Metabolic Syndrome.

In some embodiments, the Metabolic Syndrome is associated with resistance to insulin-mediated glucose uptake, glucose intolerance, hyperinsulemia, increased LDL-cholesterol, increased VLDL, increased triglycerides, decreased HDL-cholesterol, increased plasminogen activator inhibitor-1 (PAI-1) levels and hypertension. In certain embodiments, Metabolic Syndrome is characterized by three or more of the following criteria: (a) abdominal obesity: waist circumference >102 cm in men and >88 cm in women; (b) hypertriglyceridemia: ≥150 mg/dl (1.695 mmol/l); (c) low HDL cholesterol: <40 mg/dl (1.036 mmol/l) in men and <50 mg/dl (1.295 mmol/l) in women; (d) high blood pressure: ≥130/85 mm Hg; and (e) high fasting glucose: ≥110 mg/dl (>6.1 mmol/l).

In some embodiments, Metabolic Syndrome is characterized by diabetes, impaired glucose tolerance, impaired fasting glucose, or insulin resistance plus two or more of the following abnormalities: (a) high blood pressure: ≥160/90 mm Hg; (b) hyperlipidemia: triglyceride concentration ≥150 mg/dl (1.695 mmol/l) and/or HDL cholesterol <35 mg/dl (0.9 mmol/l) in men and <39 mg/dl (1.0 mmol/l) in women; (c) central obesity: waist-to-hip ratio of >0.90 in men or >0.85 in women or BMI >30 kg/m$^2$; and (d) microalbuminuria: urinary albumin excretion rate ≥20 µg/min or an albumin to creatinine ratio ≥20 mg/g.

In certain embodiments, Metabolic Syndrome is characterized by three or more of the following criteria: (a) triglycerides >150 mg/dl; (b) systolic blood pressure (BP) ≥130 mm Hg or diastolic blood pressure ≥85 mm Hg or on antihypertensive treatment; (c) high-density lipoprotein cholesterol <40 mg/dl; (d) fasting blood sugar (FBS) >110 mg/dl; and (e) body mass index >28.8 kg/m$^2$.

The compositions disclosed herein promote glucose uptake into cells.

Components of the Formulations of the Present Technology

Lipoic acid is a naturally occurring substance found in the R form, which is considered the active species. The S form of lipoic acid is produced during chemical synthesis and while having some antioxidant properties, is considered to be inactive and toxic. It can be produced from octanoic acid in cells and can become covalently attached to enzyme subunits. Lipoic acid is an essential cofactor for a variety of dehydrogenase enzyme systems in the mitochondria and plays an important role in the regulation of insulin receptor activity, glucose uptake and metabolism. Alpha Lipoic Acid (ALA) (1,2-dithione-3-pentanoic acid), known as dihydrolipoic acid (DHLA) in its reduced form, is a sulfur-containing saturated fatty acid found in small amounts in red meat, organ meats, spinach, broccoli, peas, Brussels sprouts, potatoes, yams, carrots, beets, and yeast. As a supplement, ALA is rapidly absorbed into the blood and the cells where it is reduced to DHLA by NADH or NADPH in most tissues. ALA is also synthesized de novo from octanoic acid in mitochondria. ALA occurs naturally in every cell of the body and is an essential cofactor for the mitochondrial dehydrogenase complexes which regulate mammalian glucose homoeostasis.

The quaternary ammonium compound N-acetyl-L-carnitine is involved in transporting fatty acids into mitochondria so that they can be used as a fuel for energy production. The acetyl group of N-acetyl-L-carnitine is used to form acetyl-CoA, an intermediary in the tricarboxylic acid (TCA) cycle that is used to generate energy from amino acids, fats, and carbohydrates.

Coenzyme Q10, also known as ubiquinone, ubidecarenone, coenzyme Q (CoQ10, CoQ, Q10, or Q), has been shown to improve brain and muscle energy metabolism in the electron transfer process and plays a role in the permeability of the inner mitochondrial membrane. (Alfredo Bianchi et al., Vitamins and Hormones, Vol. 69 2004 p. 297-312). The two electron oxidation of NADH in the electron transport chain is performed by coenzyme Q10 located in the mitochondrion membrane. The subsequent reduction of CoQ10 generates a proton gradient that strengthens the electron transfer chain, increasing not only the fat synthesis pathway through lipogenesis, but also increasing the overall efficiency of the TCA cycle.

L-Glutamine is an alternate carbon source to glucose in the TCA cycle, replenishing the cycle by oxidation of fatty acids to acetyl CoA.

L-arginine feeds into signal pathways of the TCA cycle. It is the immediate precursor of nitric oxide, an important cellular signaling molecule involved in many physiological and pathological processes. L-arginine is a powerful vasodilator, decreasing blood pressure and reducing atherosclerotic plaque that is associated with Metabolic Syndrome.

In some embodiments, the vitamin D compound formulations of the present technology comprise molecules such as 5-HT (5-hydroxytryptamine), tryptophan, serotonin, melatonin, their analogues and precursors as well as inhibitors of their degradation so as to promote sleep in the subject.

Vitamin D enhances the absorption of essential minerals such as calcium, phosphorous, iron, magnesium and zinc. Supplementation of vitamin D during rest allows the body to restore and heal naturally.

Methylsulfonylmethane is a natural source of biologically active sulfur.

Chamomile powder derived from flowers, seeds, and pollen may be included in the vitamin D compound formulations of the present technology.

The hormone melatonin is produced by the pineal gland among other tissues and is useful in the phase-dependent treatment of delayed sleep phase syndrome See Mundey K, Benloucif S, Harsanyi K, Dubocovich M L, and Zee P C (2005). Phase-dependent treatment of delayed sleep phase syndrome with melatonin. *Sleep* 28:1271-1278.

5-HTP (5-hydroxytryptophan), also known as oxitriptan, is a naturally occurring amino acid, chemical precursor as well as a metabolic intermediate in the biosynthesis of the neurotransmitter serotonin.

Valerian is an extract of the roots of valerian plant (*Valeriana officinalis*, Caprifoliaceae) (available at a number of commercial vendors including, but not limited to, Parchem, New Rochelle, N.Y., USA and Nutra Green, China).

Formulations of the Present Technology

The present disclosure provides therapeutic formulations intended to improve glucose uptake and the oxidation of nutrients in mammals, including humans. The thiol-containing alkyl fatty acid formulations of the present technology comprise a thiol-containing alkyl fatty acid, co-formulated with anti-oxidants, nitrogen donors, TCA cycle intermediates and herbal extracts and excipients. Additionally or alternatively, in some embodiments, thiol-containing alkyl fatty acids are co-formulated with naturally-occurring or synthetic antioxidants, amino acids, peptides, protease inhibitors, trace elements, botanical extracts, and carbohydrates.

In one aspect, the present technology provides thiol-containing alkyl fatty acid formulations comprising a thiol-containing alkyl fatty acid, a N-acetyl-L-carnitine derivative, an antioxidant, and at least one amino acid. In certain embodiments, the thiol-containing alkyl fatty acid is lipoic acid or alpha-lipoic acid. In certain embodiments, the lipoic acid or alpha-lipoic acid is an R isomer, S isomer, or a mixture of both R and S isomers. Additionally or alternatively, in some embodiments, the N-acetyl-L-carnitine derivative is L-carnitine. In certain embodiments, the amino acid is selected from among L-Glutamine and L-Arginine.

In some embodiments, the thiol-containing alkyl fatty acid is a compound having the general formula:

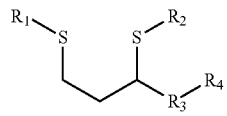

or derivatives, congeners, metallic coordination complexes and salts thereof, wherein $R_3$ is an alkyl defined as $C_nH_{2n+2}$, an alkenyl defined as $C_nH_{2n}$, and/or an alkynyl defined as $C_n$, where n is 1 to 18;

wherein $R_1$ and/or $R_2$ is aryl and/or aromatic;

wherein $R_4$, is an alkyl, alkenyl, alkynyl, aryl, —COOH, —OH, or —NH$_2$; and wherein $R_1$, $R_2$, $R_3$, and/or $R_4$ is optionally phosphorylated.

In some embodiments, the N-acetyl-L-carnitine derivative is a compound having the general formula:

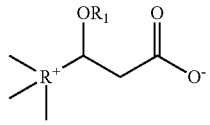

or derivatives, congeners, metallic coordination complexes and salts thereof, wherein R is N or sulfonium;

and wherein $R_1$ is H; an alkyl defined as $C_nH2_{n+2}$, an alkenyl defined as $C_nH_{2n}$, and/or an alkynyl defined as $C_n$, where n is 1 to 18; aryl; aromatic; —COOH; or —NH$_2$. In certain embodiments, the derivative is propionyl L-carnitine.

Additionally or alternatively, in some embodiments, the antioxidant is CoQ10, quercetin, or other plant-derived flavonoids.

Additionally or alternatively, in some embodiments, the amino acids are selected from among N-acetyl-L-carnitine and/or derivatives thereof, propionyl L-carnitine, L-carnitine, L-tartarate, L-glutamine, L-theanine and analogs thereof, L-arginine, and analogs thereof, and "essential" amino acids, precursors, analogs, and metabolites thereof.

In any of the above embodiments, the thiol-containing alkyl fatty acid formulations further comprise melatonin, peptides, protease inhibitors, trace elements, botanical extracts, and carbohydrates. In some embodiments, the proteins or peptides include serratiopeptidase, and/or analogs, congeners, and mimetics thereof. In certain embodiments, the trace elements include indium sulfate. In some embodiments, the plant extracts include eggplant extract, resveratrol-containing extracts such as grape and grape seed extracts, guaraná extract, purified or synthetic whole-plant cannabis extract, vanilla extract, cinnamon, nutmeg, cloves, and turmeric. These botanical extracts are commercially available at a number of suppliers (e.g., Parchem, New Rochelle, N.Y., USA; Starwest Botanicals, Sacramento, Calif.). It is anticipated that botanical extracts obtained from any supplier will be useful in the preparation of the formulations of the present technology. In some embodiments, the protease inhibitor is soybean trypsin inhibitor, leupeptin, pepstatin, or analogues, derivatives, mimetics and/or a combination thereof. In some embodiments, the carbohydrates are selected from among beta-glucans, fiber extracts, pulps, simple and complex sugars and analogs thereof. In certain embodiments, the beta-glucan is β-1,3-glucan or β-1,6-glucan.

In some embodiments, the thiol-containing alkyl fatty acid formulation comprises a wt % from about 1% to about 5%, from about 5% to about 20%, from about 20% to about 30%, or at least about 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, or 65% of a thiol-containing alkyl fatty acid, such as lipoic acid or alpha-lipoic acid, relative to all of the components of the formulation.

In some embodiments, the thiol-containing alkyl fatty acid formulation comprises a wt % from about 1% to about 5%, from about 5% to about 20%, from about 20% to about 30%, or at least about 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, or 65% of an N-acetyl L-carnitine derivative, such as L-carnitine, relative to all of the components of the formulation.

In some embodiments, the thiol-containing alkyl fatty acid formulation comprises a wt % from about 1% to about 5%, from about 5% to about 20%, from about 20% to about 30%, or at least about 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, or 65% of an antioxidant, such as CoQ10, relative to all of the components of the formulation.

In some embodiments, the thiol-containing alkyl fatty acid formulation comprises a wt % from about 1% to about 5%, from about 5% to about 20%, from about 20% to about 30%, or at least about 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, or 65% of an amino acid, such as L-Glutamine or L-Arginine, relative to all of the components of the formulation.

In some embodiments, the ratio of the thiol-containing alkyl fatty acid (e.g., alpha-lipoic acid) to the N-acetyl L-carnitine derivative (e.g., L-carnitine) in the thiol-containing alkyl fatty acid formulation of the present technology is about 2:1, 1.9:1, 1.8:1, 1.6:1, 1.5:1, 1.4:1, 1.3:1, 1.2:1 or 1.1:1.

In some embodiments, the ratio of the thiol-containing alkyl fatty acid (e.g., alpha-lipoic acid) to the antioxidant (e.g., CoQ10) in the thiol-containing alkyl fatty acid formulation of the present technology is about 8:1, 7:1, 6.5:1, 6:1, 5.5:1, 5:1, 4:1 or 3:1.

In some embodiments, the ratio of the thiol-containing alkyl fatty acid (e.g., alpha-lipoic acid) to the amino acid (e.g., L-Glutamine or L-Arginine) in the thiol-containing alkyl fatty acid formulation of the present technology is about 1:1, 1:1.1, 1:1.25, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, or 1:3.

Additionally or alternatively, the thiol-containing alkyl fatty acid, the N-acetyl-L-carnitine derivative, the antioxidant, or the at least one amino acid is present in a thiol-containing alkyl fatty acid formulation useful in accordance with methods described herein in an amount of from about 50 mg to about 100 mg, or from about 100 mg to about 150 mg, or from about 150 mg to about 200 mg, or from about 200 mg to about 250 mg, or from about 300 mg to about 350 mg, or from about 400 mg to about 450 mg, or from about 450 mg to about 500 mg, or from about 500 mg to about 600 mg, or from about 600 mg to about 800 mg, or from about 800 mg to about 1,000 mg, or from about 1,000 mg to about 1,200 mg, or from about 1,200 mg to about 1,400 mg, or from about 1,400 mg to about 1,600 mg, or from about 1,600 mg to about 1,800 mg, or from about 1,800 mg to about 2,000 mg, or from about 2,000 mg to about 2,200 mg, or from about 2,200 mg to about 2,500 mg.

Also provided herein are vitamin D compound formulations comprising amino acids, peptides, nucleic acids, carbohydrates, vitamins, other organic molecules and trace elements and plant extracts.

In one aspect, the present technology provides vitamin D compound formulations comprising a vitamin D compound, a sulfur donor and one or more sedatives or sleep promoting agents. In some embodiments, the vitamin D compound is cholecalciferol (D3), ergocalciferol (D2) or other vitamin D analogs. Additionally or alternatively, in some embodiments, the sulfur donor is methylsulfonylmethane.

Additionally or alternatively, in some embodiments, the sedatives or sleep promoting agents are one or more of melatonin, chamomile extract, valerian extract, 5-hydroxytryptamine (5-HT), 5HTP (L-5-hydroxytryptophan), L-theanine, D-phenylalanine, L-phenylalanine, or a mixture of D- and L-phenylalanine.

Additionally or alternatively, in some embodiments, the vitamin D compound formulations of the present technology further comprise peptides, proteins, trace elements, plant extracts, protease inhibitors, and carbohydrates. In some embodiments, the proteins or peptides include serratiopeptidase, and/or analogs, congeners, and mimetics thereof. In certain embodiments, the trace elements include indium sulfate. In some embodiments, the plant extracts include eggplant extract, resveratrol-containing extracts such as grape and grape seed extracts, guaraná extract, purified or synthetic whole-plant cannabis extract, vanilla extract, cinnamon, nutmeg, cloves, and turmeric. These botanical extracts are commercially available at a number of suppliers (e.g., Parchem, New Rochelle, N.Y., USA; Starwest Botanicals, Sacramento, Calif.). It is anticipated that botanical extracts obtained from any supplier will be useful in the preparation of the formulations of the present technology. In some embodiments, the protease inhibitor is soybean trypsin inhibitor, leupeptin, pepstatin, or analogues, derivatives, mimetics and/or a combination thereof. In some embodiments, the carbohydrates are selected from among beta-glucans, fiber extracts, pulps, simple and complex sugars and analogs thereof. In certain embodiments, the beta-glucan is β-1,3-glucan or β-1,6-glucan.

Additionally or alternatively, the sulfur donor, or the one or more sedatives or sleep promoting agents is present in a vitamin D compound formulation useful in accordance with methods described herein in an amount of from about 1 mg to about 10 mg, from about 10 mg to about 50 mg, from about 50 mg to about 100 mg, or from about 100 mg to about 150 mg, or from about 150 mg to about 200 mg, or from about 200 mg to about 250 mg, or from about 300 mg to about 350 mg, or from about 400 mg to about 450 mg, or from about 450 mg to about 500 mg, or from about 500 mg to about 600 mg, or from about 600 mg to about 800 mg, or from about 800 mg to about 1,000 mg.

In some embodiments, the vitamin D compound formulations disclosed herein restore or enhance the body's own ability to adjust hormone levels and metabolic function during sleep. In certain embodiments, the sleep inducing and enhancing components are formulated in a controlled release formulation such that (1) the sedating and sleep inducing components such as chamomile and melatonin are released immediately, (2) the sleep maintaining components such as 5-HTP are slowly released over time, maintaining a consistent blood level through the sleep period and (3) the REM promoting components, such as valerian is delayed released to initial the REM sleep cycle appropriately. In yet a further example embodiment, a bronchial dilator is combined with the sleep inducing and enhancing components to prevent or reduce sleep apnea.

In any of the above embodiments, the thiol-containing alkyl fatty acid formulations and vitamin D compound formulations of the present technology may include pharmaceutically acceptable carriers and excipients.

In any of the above embodiments, at least two, at least three, or at least four or more of the individual components of the thiol-containing alkyl fatty acid formulations and vitamin D compound formulations of the present technology have overlapping oral bioavailability.

Additionally or alternatively, the thiol-containing alkyl fatty acid formulations and vitamin D compound formulations of the present technology may be provided as an oral solid medicament in the form of tablets, capsules, powders, nanoparticles, or nano-emulsions for immediate or sustained release. The thiol-containing alkyl fatty acid formulations and vitamin D compound formulations of the present technology may comprise a plurality of crystalline structures. The thiol-containing alkyl fatty acid formulations and vitamin D compound formulations can also contain additional ingredients or encapsulations that establish the release profile of each or the collective ingredient(s) for instantaneous release, or sustained release. In a further embodiment, the oral solid dosage form can be enterically coated so as to prevent gastric irritation in the subject. Alternatively, the thiol-containing alkyl fatty acid formulations and vitamin D compound formulations of the present technology can be either fully dissolved or prepared as an emulsion. Additionally or alternatively, the thiol-containing alkyl fatty acid formulations and vitamin D compound formulations of the present technology may be provided as a liquid.

In another aspect, the thiol-containing alkyl fatty acid formulations and vitamin D compound formulations of the present technology comprise acid analogs of the components disclosed herein, which are buffered by ion-pairing salts to minimize rapid degradation, increase absorption, and to minimize stomach irritation or acid reflux.

The present disclosure thus provides a diurnal regimen comprising a thiol-containing alkyl fatty acid formulation and a vitamin D compound formulation.

Therapeutic Methods

The following discussion is presented by way of example only, and is not intended to be limiting. The present technology also provides methods of using the formulations disclosed herein to prevent or treat diabetes, pre-diabetes, Metabolic Syndrome.

One aspect of the present technology includes methods of treating pre-diabetes, diabetes or Metabolic Syndrome in a subject diagnosed as having, suspected as having, or at risk of having pre-diabetes, diabetes or Metabolic Syndrome. In therapeutic applications, formulations of the present technology are administered to a subject suspected of, or already suffering from such a disease (such as, e.g., subjects with IFG and/or IGT, insulin resistance or elevated glycated hemoglobin levels (HbA1c) or a subject diagnosed with pre-diabetes, diabetes or Metabolic Syndrome), in an amount sufficient to cure, or at least partially arrest, the symptoms of the disease, including its complications and intermediate pathological phenotypes in development of the disease.

Subjects suffering from pre-diabetes, diabetes or Metabolic Syndrome can be identified by any or a combination of diagnostic or prognostic assays known in the art (e.g., fasting glucose or glucose tolerance, liver and pancreas laboratory panels and levels of glycosylated hemoglobin). In addition to height, weight, blood pressure, cardiovascular and pulmonary functions, body mass index (BMI) has emerged as a likely indicator of metabolic dysfunction (see journals.plos.org/plosmedicine/article?id=10.1371/journal.pmed.1001230#). Body waist size may correlate with the risk of type II diabetes.

For example, typical symptoms of pre-diabetes, diabetes or Metabolic Syndrome include, but are not limited to, body weight, fasting glucose/insulin/free fatty acid, glucose tolerance (OGTT), muscle insulin sensitivity, markers of insulin signaling (e.g., Akt-P, IRS-P), serum triglyceride levels, HDL and LDL cholesterol levels, blood pressure, serum fibrinogen or plasminogen activator inhibitor levels, levels of C-reactive protein, insulin resistance, glucose intolerance, elevated levels of glycosylated blood proteins (e.g., hemoglobin).

In some embodiments, pre-diabetic, diabetic or Metabolic Syndrome subjects treated with the formulation of the present technology will show amelioration or elimination of one or more of the following symptoms: body weight, fasting glucose/insulin/free fatty acid, glucose tolerance (OGTT), muscle insulin sensitivity, markers of insulin signaling (e.g., Akt-P, IRS-P), serum triglyceride levels, HDL and LDL cholesterol levels, blood pressure, serum fibrinogen or plasminogen activator inhibitor levels, levels of C-reactive protein, insulin resistance, glucose intolerance, elevated levels of glycosylated blood proteins (e.g., hemoglobin).

In some embodiments of the methods of the present technology, Metabolic Syndrome is treated through improvement of lipid metabolism compared to the subject's lipid metabolism before being administered the formulations disclosed herein. In one embodiment, the improvement in lipid metabolism is reduction of blood triglyceride level compared to the subject's blood triglyceride level before being administered the formulations of the present technology. In another embodiment, the improvement in lipid metabolism is improvement of blood HDL/LDL cholesterol ratio compared to the subject's blood HDL/LDL cholesterol before being administered the formulations of the present technology. For instance, a subject may exhibit at least about 5%, at least about 10%, at least about 20%, or at least about 50% reduction in body weight compared to the subject prior to receiving the formulations of the present technology. In one embodiment, a subject may exhibit at least about 5%, at least about 10%, at least about 20%, or at least about 50% reduction in HDL cholesterol and/or at least about 5%, at least about 10%, at least about 20%, or at least about 50% increase in LDL cholesterol compared to the subject prior to receiving the formulations of the present technology. In one embodiment, a subject may exhibit at least about 5%, at least about 10%, at least about 20%, or at least about 50% reduction in serum triglycerides compared to the subject prior to receiving the formulations of the present technology. In one embodiment, a subject may exhibit at least about 5%, at least about 10%, at least about 20%, or at least about 50% improvement in oral glucose tolerance (OGTT) compared to the subject prior to receiving the formulations of the present technology.

Additionally or alternatively, in some embodiments of the methods of the present technology, Metabolic Syndrome is treated by reducing blood sugar level compared to the subject's blood sugar level before being administered the formulations of the present technology. In other embodiments, Metabolic Syndrome is treated by a reduction in body weight compared to the subject's body weight before being administered the formulations of the present technology.

In some cases, the insulin resistance may be due to a high fat diet or, more generally, over-nutrition. The formulations of the present technology are useful in treating diabetic, pre-diabetic or obese insulin resistant, non-diabetic patients. Insulin resistance occurs when the body does not respond to the insulin made by the pancreas and glucose is less able to enter the cells. Subjects with insulin resistance may or may not go on to develop type 2 diabetes. In some embodiments, administration of an effective amount of the formulations of the present technology improves at least one sign or symptom of insulin resistance in the subject, e.g., body weight, fasting glucose/insulin/free fatty acid, glucose tolerance (OGTT), in vitro muscle insulin sensitivity, markers of insulin signaling (e.g., Akt-P, IRS-P), mitochondrial function (e.g., respiration), mitochondrial enzyme activity and the like.

Also provided are methods for treating a disease or condition characterized by elevated glycated hemoglobin levels (HbA1c) in a subject in need thereof comprising administering to the subject an effective amount of the formulations of the present technology to the subject. In some embodiments, administration of an effective amount of the formulations of the present technology causes a reduction in the glycated hemoglobin levels (HbA1c) of the subject. In some embodiments, the disease or condition characterized by elevated glycated hemoglobin levels (HbA1c) is pre-diabetes, diabetes, Metabolic Syndrome, insulin resistance, glucose intolerance or cardiovascular disease, and stroke. In some embodiments, administration of an effective amount of the formulations of the present technology causes a reduction in the glycated hemoglobin levels (HbA1c) of the subject by at least 3%, by at least 4%, by at least 5%, by at least 6%, by at least 8%, or by at least 10% compared to that observed in the subject prior to treatment.

Prophylactic Methods

In one aspect, the present technology provides a method for preventing or delaying the onset of pre-diabetes, diabetes or Metabolic Syndrome or symptoms of pre-diabetes, diabetes or Metabolic Syndrome in a subject at risk of having pre-diabetes, diabetes or Metabolic Syndrome. In some embodiments, the subject may exhibit IFG and/or IGT, insulin resistance, and/or elevated glycated hemoglobin levels (HbA1c).

Subjects suffering from pre-diabetes, diabetes or Metabolic Syndrome can be identified by, e.g., any or a combination of diagnostic or prognostic assays known in the art. In prophylactic applications, the formulations of the present technology are administered to a subject susceptible to, or otherwise at risk of a disease or condition such as e.g., pre-diabetes, diabetes or Metabolic Syndrome, in an amount sufficient to eliminate or reduce the risk, or delay the onset of the disease, including biochemical, histologic and/or behavioral symptoms of the disease, its complications and intermediate pathological phenotypes presenting during development of the disease. Administration of a prophylactic formulation of the present technology can occur prior to the manifestation of symptoms characteristic of the disease or disorder, such that the disease or disorder is prevented or, alternatively, delayed in its progression.

For therapeutic and/or prophylactic applications, one or more formulations of the present technology are administered to the subject. In some embodiments, the thiol-containing alkyl fatty acid formulations and vitamin D compound formulations are administered one, two, three, four, or five times per day. In some embodiments, the thiol-containing alkyl fatty acid formulations and vitamin D compound formulations are administered more than five times per day. Additionally or alternatively, in some embodiments, the thiol-containing alkyl fatty acid formulations and vitamin D compound formulations are administered every day, every other day, every third day, every fourth day, every fifth day, or every sixth day. In some embodiments, the thiol-containing alkyl fatty acid formulations and vitamin D compound formulations are administered weekly, bi-weekly, tri-weekly, or monthly. In some embodiments, the thiol-containing alkyl fatty acid formulations and vitamin D compound formulations are administered for a period of one, two, three, four, or five weeks. In some embodiments, the thiol-containing alkyl fatty acid formulations and vitamin D compound formulations are administered for six weeks or more. In some embodiments, the thiol-containing alkyl fatty acid formulations and vitamin D compound formulations are administered for twelve weeks or more. In some embodiments, the thiol-containing alkyl fatty acid formulations and vitamin D compound formulations are administered for a period of less than one year. In some embodiments, the thiol-containing alkyl fatty acid formulations and vitamin D compound formulations are administered for a period of more than one year. In some embodiments, the thiol-containing alkyl fatty acid formulations and vitamin D compound formulations of the present technology are administered orally, topically, intranasally, systemically, intravenously, subcutaneously, intraperitoneally, intradermally, iontophoretically, transmucosally, or intramuscularly.

In some embodiments of the methods of the present technology, the thiol-containing alkyl fatty acid formulations and vitamin D compound formulations of the present technology are administered daily for 1 week or more. In some embodiments of the methods of the present technology, the thiol-containing alkyl fatty acid formulations and vitamin D compound formulations of the present technology are administered daily for 2 weeks or more. In some embodiments of the methods of the present technology, the thiol-containing alkyl fatty acid formulations and vitamin D compound formulations of the present technology are administered daily for 3 weeks or more. In some embodiments of the methods of the present technology, the thiol-containing alkyl fatty acid formulations and vitamin D compound formulations of the present technology are administered daily for 4 weeks or more. In some embodiments of the methods of the present technology, the thiol-containing alkyl fatty acid formulations and vitamin D compound formulations of the present technology are administered daily for 6 weeks or more. In some embodiments of the methods of the present technology, the thiol-containing alkyl fatty acid formulations and vitamin D compound formulations of the present technology are administered daily for 12 weeks or more.

In some embodiments, treatment with the thiol-containing alkyl fatty acid formulations and vitamin D compound formulations of the present technology will prevent or delay the onset of one or more of the following symptoms: increased body weight, elevated serum triglyceride levels, decreased HDL and/or increased LDL cholesterol levels, high blood pressure, insulin resistance, glucose intolerance, elevated levels of glycosylated blood proteins (e.g., hemoglobin), alterations in one or more of the following compared to healthy control subjects—fasting glucose/insulin/free fatty acid, glucose tolerance (OGTT), muscle insulin sensitivity, markers of insulin signaling (e.g., Akt-P, IRS-P), serum fibrinogen or plasminogen activator inhibitor levels, levels of C-reactive protein, etc.

EXAMPLES

The present technology is further illustrated by the following examples, which should not be construed as limiting in any way. For each of the examples below, any formulation as described herein could be used.

Example 1

Methods of Treatment Using Formulation A and Formulation B

This Example demonstrates that the formulations of the present technology are useful in treating pre-diabetes, diabetes or Metabolic Syndrome in human subjects. Many of the individual components of the disclosed formulations are commercially available at a number of suppliers. The suppliers disclosed herein are intended to be exemplary. It is anticipated that there are multiple commercial sources for the individual components of the compositions of the present technology useful in the preparation of the formulations of the present technology.

Compositions

Formulation A is an example of a thiol-containing alkyl fatty acid formulation for the treatment of pre-diabetes, diabetes, Metabolic Syndrome or a disease characterized by abnormal glucose metabolism.

The components of Formulation A are lipoic acid, L-carnitine, CoQ10, L-glutamine and L-arginine. One advantage of this formulation is the availability of arginine as a nitric oxide donor in the presence of glutamine, a carbon source for mitochondrial function and a neurotransmitter precursor.

| Formulation A | |
| --- | --- |
| Ingredient | Amount |
| Alpha-lipoic acid (Changshu Wanxing Chemical Co. Ltd., China) | 600 mg |
| L-Carnitine (Kaiyuan Hengtai Chemical Co., Ltd. China) | 400 mg |
| CoQ10 (Inner Mongolia Kingdomway Pharmaceuticals Co., Ltd., China) | 100 mg |
| L-Glutamine (Kyowa Hakko Kogyo Co., Japan) | 750 mg |
| L-Arginine (Shine Star (Hubei) Biological Engineering Co., Ltd., China) | 1500 mg |

The components of Formulation A are both allosteric regulators (prosthetic groups for selected enzymes, genetic and epigenetic stimulators of activity), and regulators of transport molecules that convey glucose, lipids, and fatty acids to the mitochondria. Without wishing to be bound by theory, the net result may be an increased ability to transport glucose out of the blood and into tissues independent of insulin levels.

Further, over the course of treatment, levels of glucose transporter proteins may be increased.

Formulation B is an example of a vitamin D compound formulation for the treatment of pre-diabetes, diabetes, Metabolic Syndrome or a disease characterized by abnormal glucose metabolism.

| Formulation B | |
|---|---|
| Ingredient | Amount |
| Vitamin D (Prinova Solutions, Carol Stream, IL, USA) | 1000 IU |
| Methylsulfonylmethane (e.g., Foodchem International Corporation, China) | 400 mg |
| 5-HTP (*Gryffonia simplicfolia* seed) (Jiangsu Swellxin Biopharm Pty. Ltd., China) | 50 mg |
| Melatonin (Wuhan Yuancheng Technology Development Co., Ltd., China) | 3 mg |
| Valerian root powder (e.g., Parchem, New Rochelle, New York, USA) | 600 mg |
| Chamomile powder (isolated from flowers, seeds, pollen) (e.g., Parchem, New Rochelle, New York, USA) | 500 mg |
| L-Theanine (Sichuan Tongsheng Amino Acid Co., Ltd., China) | 400 mg |

Methods

Three male patients received a daily dose of Formulation A and Formulation B for 90 days. BMI, heart rate, blood pressure, and HbA1c levels were measured prior to treatment (Day 0) and 90 days post administration of Formulation A and Formulation B. See Tables 1 and 2.

TABLE 1

| | | Heart Rate | | Blood Pressure | | HbA1c 1 | |
|---|---|---|---|---|---|---|---|
| Patient | Age | Day 0 | Day 90 | Day 0 | Day 90 | Day 0 | Day 90 |
| 1 | 76 | 92 | 70 | 112/75 | 120/80 | 7.0 | 6.7 |
| 2 | 90 | 70 | 66 | 155/75 | 150/70 | 6.1 | 5.8 |
| 3 | 47 | N/a | N/a | 135/90 | 128/86 | 5.7 | 5.8 |

HbA1c levels can indicate people with pre-diabetes or diabetes—Specifically, the HbA1c in normal subjects is below 6.0%, whereas the HbA1c is 6.0-6.4% in pre-diabetic subjects and ≥6.5% in diabetic subjects. As shown in Table 1, patients 1 and 2 exhibited an observable reduction in HbA1c after receiving a daily dose of Formulations A and B for 90 days. Further, patient 1 showed a reduction in the severity of pre-diabetes whereas patient 2, which initially had pre-diabetic HbA1c levels, exhibited normal HbA1c level post-treatment. HbA1c levels can also be used to predict the estimated average blood glucose (mg/dL). See FIG. 1. The estimated average blood glucose for patient 1 and patient 2 post-treatment are 146 mg/dL and 120 mg/dL respectively. Both patient 1 and patient 2 showed a 8 mg/dL decrease in the estimated average blood glucose at the end of the 90 day treatment window, which corresponds to a 5.2% and 6.2% decrease in estimated average blood glucose in patient 1 and patient 2 respectively.

Table 1 also shows that administration of Formulations A and B improved heart rate and blood pressure in some patients.

TABLE 2

| | | Weight | | BMI | |
|---|---|---|---|---|---|
| Patient | Height | Day 0 | Day 90 | Day 0 | Day 90 |
| 1 | 67.0 | 164 | 159 | 25.7 | 24.1 |
| 2 | 68.5 | 166.0 | 168.5 | 24.9 | 25.2 |
| 3 | 72.0 | 218 | 213 | 29.6 | 28.9 |

TABLE 3

| BMI | Weight Status |
|---|---|
| Below 18.5 | Underweight |
| 18.5-24.9 | Normal or Healthy Weight |
| 25.0-29.9 | Overweight |
| 30.0 and Above | Obese |

As shown in Tables 2 and 3, patient 1 showed about a 7% decrease in BMI and a change in weight status from "overweight" to a "healthy weight" at the end of the 90 day treatment window. Table 2 shows that patient 3 exhibited a mild improvement in BMI at the end of the 90 day treatment window. No adverse events were reported. One out of the three patients showed a dramatic improvement in restorative sleep.

These results demonstrate that the thiol-containing alkyl fatty acid formulations and vitamin D compound formulations of the present technology are effective in reducing elevated levels of glycated hemoglobin (HbA1c) in mammalian subjects. Accordingly, the thiol-containing alkyl fatty acid formulations and vitamin D compound formulations disclosed herein are useful for treating pre-diabetes, diabetes, Metabolic Syndrome or a condition associated with abnormal glucose metabolism in a subject in need thereof.

Example 2

Treatment of Diabetes as Measured by Reduction in HbA1c

This Example will show that the formulations of the present technology are useful in the treatment of diabetes.

Methods

Animals: Male mice (ddY, 5 weeks old) are kept in an experimental animal room for 7 days with free access to food and water. Neonatal streptozotocin-induced diabetic mice (NSZ) are produced by subcutaneous injection of streptozotocin (STZ), 90 mg/kg body weight, which is dissolved in citrate buffer (pH 4.5). Non-STZ injected mice are used as a control. Five weeks after injection of STZ, the blood glucose level of all the mice are determined. Mice with a blood glucose level above 250 mg/dl are considered to be diabetic and are used in the study.

Determination of Glucose and Hemoglobin A1c (HbA1c): To identify diabetic mice, blood samples are withdrawn from the cavernous sinus with a capillary in STZ treated mice and blood glucose levels are determined by the glucose oxidase method.

HbA1c levels are measured from blood samples from test subjects by an immunoassay (see, e.g., DCA-2000 System, Bayer-Sankyo Co., Ltd. Tokyo, Japan).

Treatment: The mice are divided into groups and treated according to Tables 4-7 (see Example 1 for composition of Formulation A and Formulation B):

TABLE 4

Diabetic Mice First Treatment

| Group | Treatment |
|---|---|
| 1 | Untreated |
| 2 | Formulation A |
| 3 | Alpha-lipoic acid (Changshu Wanxing Chemical Co. Ltd., China) |
| 4 | L-Carnitine (Kaiyuan Hengtai Chemical Co., Ltd. China) |
| 5 | CoQ10 (Inner Mongolia Kingdomway Pharmaceuticals Co., Ltd., China) |
| 6 | L-Glutamine (Kyowa Hakko Kogyo Co., Japan) |
| 7 | L-Arginine (Shine Star (Hubei) Biological Engineering Co., Ltd., China) |
| 8 | Vitamin D (Prinova Solutions, Carol Stream, IL, USA) |
| 9 | Methylsulfonylmethane (e.g., Foodchem International Corporation, China) |
| 10 | 5-HTP (*Gryffonia simplicfolia* seed) (Jiangsu Swellxin Bio-pharm Pty. Ltd., China) |
| 11 | Melatonin (Wuhan Yuancheng Technology Development Co., Ltd., China) |
| 12 | Valerian root powder (e.g., Parchem, New Rochelle, New York, USA) |
| 13 | Chamomile powder (isolated from flowers, seeds, pollen) (e.g., Parchem, New Rochelle, New York, USA) |
| 14 | L-Theanine (Sichuan Tongsheng Amino Acid Co., Ltd., China) |

TABLE 5

Control Mice First Treatment

| Group | Treatment |
|---|---|
| 15 | Untreated |
| 16 | Formulation A |
| 17 | Alpha-lipoic acid (Changshu Wanxing Chemical Co. Ltd., China) |
| 18 | L-Carnitine (Kaiyuan Hengtai Chemical Co., Ltd. China) |
| 19 | CoQ10 (Inner Mongolia Kingdomway Pharmaceuticals Co., Ltd., China) |
| 20 | L-Glutamine (Kyowa Hakko Kogyo Co., Japan) |
| 21 | L-Arginine (Shine Star (Hubei) Biological Engineering Co., Ltd., China) |
| 22 | Vitamin D (Prinova Solutions, Carol Stream, IL, USA) |
| 23 | Methylsulfonylmethane (e.g., Foodchem International Corporation, China) |
| 24 | 5-HTP (*Gryffonia simplicfolia* seed) (Jiangsu Swellxin Bio-pharm Pty. Ltd., China) |
| 25 | Melatonin (Wuhan Yuancheng Technology Development Co., Ltd., China) |
| 26 | Valerian root powder (e.g., Parchem, New Rochelle, New York, USA) |
| 27 | Chamomile powder (isolated from flowers, seeds, pollen) (e.g., Parchem, New Rochelle, New York, USA) |
| 28 | L-Theanine (Sichuan Tongsheng Amino Acid Co., Ltd., China) |

TABLE 6

Diabetic Mice Second Treatment

| Group | Treatment |
|---|---|
| 1 | Untreated |
| 2 | Formulation B |
| 3 | Alpha-lipoic acid (Changshu Wanxing Chemical Co. Ltd., China) |
| 4 | L-Carnitine (Kaiyuan Hengtai Chemical Co., Ltd. China) |
| 5 | CoQ10 (Inner Mongolia Kingdomway Pharmaceuticals Co., Ltd., China) |
| 6 | L-Glutamine (Kyowa Hakko Kogyo Co., Japan) |
| 7 | L-Arginine (Shine Star (Hubei) Biological Engineering Co., Ltd., China) |
| 8 | Vitamin D (Prinova Solutions, Carol Stream, IL, USA) |
| 9 | Methylsulfonylmethane (e.g., Foodchem International Corporation, China) |
| 10 | 5-HTP (*Gryffonia simplicfolia* seed) (Jiangsu Swellxin Bio-pharm Pty. Ltd., China) |
| 11 | Melatonin (Wuhan Yuancheng Technology Development Co., Ltd., China) |
| 12 | Valerian root powder (e.g., Parchem, New Rochelle, New York, USA) |
| 13 | Chamomile powder (isolated from flowers, seeds, pollen) (e.g., Parchem, New Rochelle, New York, USA) |
| 14 | L-Theanine (Sichuan Tongsheng Amino Acid Co., Ltd., China) |

TABLE 7

Control Mice Second Treatment

| Group | Treatment |
|---|---|
| 15 | Untreated |
| 16 | Formulation B |
| 17 | Alpha-lipoic acid (Changshu Wanxing Chemical Co. Ltd., China) |
| 18 | L-Carnitine (Kaiyuan Hengtai Chemical Co., Ltd. China) |
| 19 | CoQ10 (Inner Mongolia Kingdomway Pharmaceuticals Co., Ltd., China) |
| 20 | L-Glutamine (Kyowa Hakko Kogyo Co., Japan) |
| 21 | L-Arginine (Shine Star (Hubei) Biological Engineering Co., Ltd., China) |
| 22 | Vitamin D (Prinova Solutions, Carol Stream, IL, USA) |
| 23 | Methylsulfonylmethane (e.g., Foodchem International Corporation, China) |
| 24 | 5-HTP (*Gryffonia simplicfolia* seed) (Jiangsu Swellxin Bio-pharm Pty. Ltd., China) |
| 25 | Melatonin (Wuhan Yuancheng Technology Development Co., Ltd., China) |
| 26 | Valerian root powder (e.g., Parchem, New Rochelle, New York, USA) |
| 27 | Chamomile powder (isolated from flowers, seeds, pollen) (e.g., Parchem, New Rochelle, New York, USA) |
| 28 | L-Theanine (Sichuan Tongsheng Amino Acid Co., Ltd., China) |

Each group includes 10 mice. All mice in Groups 3-14 and 17-28 are treated with their respective compound twice daily by oral administration (i.e., drinking water or gavage). All mice in Groups 2 and 16 are treated daily with Formulation A once and Formulation B once. The dosages of each formulation or compound (disclosed in Example 1) are adjusted according to the proper ratio based on the average BMI of the mice. Groups 3-14 and 17-28 are treated with an equivalent molar dose of their respective compounds based on the concentration of the respective compound (i.e., alpha-lipoic acid, L-carnitine, CoQ10, L-glutamine, L-arginine, vitamin D, methylsulfonylmethane, 5-HTP, melatonin, valerian root powder, L-theanine and chamomile powder) in Formulation A and Formulation B administered in the Formulation A/Formulation B treatment groups. All mice are treated for 90 days. Blood is drawn from each mouse at 7 days post $1^{st}$ treatment, 14 days post $1^{st}$ treatment, 28 days post $1^{st}$ treatment, 56 days post $1^{st}$ treatment, 70 days post $1^{st}$ treatment, and 90 days post $1^{st}$ treatment and the HbA1c level is determined for each blood sample.

Results

It is anticipated that diabetic mice treated with Formulation A and Formulation B will show a reduction of HbA1c as compared to the untreated diabetic control group. It is also anticipated that diabetic mice treated with Formulation A and Formulation B will show a synergistic effect by having a greater reduction of HbA1c, reduced side effects, and/or additional therapeutic benefits (including, but not limited to reduced BMI, improved heart rate and blood pressure) as compared to diabetic mice treated with the individual components of Formulation A or Formulation B alone.

These results demonstrate that the formulations of the present technology are effective in reducing elevated levels of glycated hemoglobin (HbA1c) in mammalian subjects. These results will show that Formulation A or Formulation B of the present technology are useful in methods for treating diabetes in mammalian subjects.

Example 3

Prevention or Treatment of Insulin Resistance

This Example will show that the formulations of the present technology are useful in the treatment of insulin resistance.

Methods

The fatty (fa/fa) Zucker rat, a model of diet-induced insulin resistance is used. Young Zucker rats (~3-4 weeks of age) and control wild-type rats are either untreated or administered Formulation A and Formulation B or their respective individual components as described in Tables 4-7 in Example 2 for 90 days. Two parallel experiments are conducted to test the prevention and treatment of insulin resistance.

Determination of Hemoglobin A1c (HbA1c): Blood is drawn from the subjects at 7 days post $1^{st}$ treatment, 14 days post $1^{st}$ treatment, 28 days post $1^{st}$ treatment, 56 days post $1^{st}$ treatment, 70 days post $1^{st}$ treatment, and 90 days post $1^{st}$ treatment and HbA1c level is determined for each blood sample. HbA1c is measured by an immunoassay (see, e.g., DCA-2000 System, Bayer-Sankyo Co., Ltd. Tokyo, Japan).

Results

It is anticipated that administration of Formulation A and Formulation B will attenuate or prevent the development of whole body and muscle insulin resistance that normally develops in the fatty (fa/fa) Zucker rat. Measured outcomes include body weight, fasting glucose/insulin/free fatty acid, glucose tolerance (OGTT), in vitro muscle insulin sensitivity (incubation), markers of insulin signaling (Akt-P, IRS-P), mitochondrial function studies on permeabilized fibers (respiration, $H_2O_2$ emission), and the like. A comparison is made between control rats and fa/fa rats administrated Formulation A and Formulation B. Controls include wild-type and fa/fa rats not administered Formulation A and Formulation B (i.e., the untreated rats). Successful prevention of insulin resistance by the administration of Formulation A and Formulation B is indicated by a reduction in one or more of the markers associated with insulin resistance. It is anticipated that fa/fa rats treated with Formulation A and Formulation B will show a reduction of HbA1c as compared to the untreated fa/fa control group and that HbA1c levels of fa/fa rats treated with Formulation A and Formulation B will resemble those observed in the wild-type control rats.

It is anticipated that administration of Formulation A and Formulation B will ameliorate or reduce whole body and muscle insulin resistance that normally develops in these older fatty (fa/fa) Zucker rats. Measured outcomes include body weight, fasting glucose/insulin/free fatty acid, glucose tolerance (OGTT), in vitro muscle insulin sensitivity (incubation), markers of insulin signaling (Akt-P, IRS-P), mitochondrial function studies on permeabilized fibers (respiration, $H_2O_2$ emission), and mitochondrial enzyme activity. A comparison is made between control rats and fa/fa rats administrated Formulation A and Formulation B. Controls include wild-type and fa/fa rats not administered Formulation A and Formulation B (i.e., the untreated rats). Successful treatment of insulin resistance by the administration of Formulation A and Formulation B is indicated by a reduction in one or more of the markers associated with insulin resistance. It is anticipated that fa/fa rats treated with Formulation A and Formulation B will show a reduction of HbA1c as compared to the untreated fa/fa control group and that HbA1c levels of fa/fa rats treated with Formulation A and Formulation B will resemble those observed in the wild-type control rats.

It is also anticipated that Zucker rats administered Formulation A and Formulation B will show a synergistic effect by having a greater reduction in one or more of the markers/symptoms associated with insulin resistance enumerated above and HbA1c levels as compared to Zucker rats treated with the individual components of Formulation A and Formulation B alone.

These results demonstrate that the formulations of the present technology are effective in reducing elevated levels of glycated hemoglobin (HbA1c) in mammalian subjects. These results will show that administration of Formulation A and Formulation B of the present technology are useful in methods for preventing and treating insulin resistance in mammalian subjects.

Example 4

Treatment of Metabolic Syndrome in Rats Fed a High Fat Diet

This Example will show that the formulations of the present technology are useful in the treatment of Metabolic Syndrome.

Methods

In vivo model. A rat model of Metabolic Syndrome is established by a combination of 6-week high fat diet (HFD) and low-dose STZ (40 mg/kg) injection in Sprague-Dawley rats. Rats fed with normal chow (NRC) are used as a control. Rats are grouped and treated as described in Tables 4-7 in Example 2. Metabolic Syndrome rats maintain the HFD and control rats maintain the NRC diet throughout the 90 day treatment period.

Blood glucose. Blood glucose is tested by ACCU-CHEK® Advantage™ blood glucose meter and test strips from Roche diagnostics GmbH (Mannheim, Germany).

Blood sample handling. Blood samples are collected by tail snip. In some cases when tail snip fail to provide sufficient volume, blood samples are collected from retro-orbital sinus. Collected blood samples are set at room temperature for 30 min to allow clotting before being centrifuged at 1,200×g for 10 min. The supernatant is collected and re-centrifuged at 1,200×g for another 5 min to generate the serum. Serum samples are aliquoted and stored at −20° C. until used in analysis.

Determination of Hemoglobin A1c (HbA1c): Blood is drawn from the subjects at 7 days post $1^{st}$ treatment, 14 days post $1^{st}$ treatment, 28 days post $1^{st}$ treatment, 56 days post $1^{st}$ treatment, 70 days post $1^{st}$ treatment, and 90 days post $1^{st}$ treatment and HbA1c levels are determined for each blood sample. HbA1c is measured by an immunoassay (see, e.g., DCA-2000 System, Bayer-Sankyo Co., Ltd. Tokyo, Japan).

Statistics: Statistic analysis of t-test and one-way ANOVA is performed by SPSS (Statistical Package for Social Science) analysis software.

Results

Effects of Administration of Formulation A and B on the body weight of Metabolic Syndrome rats. It is anticipated that Metabolic Syndrome rats administered Formulation A and B will have reduced body weight as compared to untreated Metabolic Syndrome rats. It is also anticipated that Metabolic Syndrome rats administered Formulation A and B will show a synergistic effect with respect to lower body weight as compared to Metabolic Syndrome rats treated with the individual components of Formulation A and Formulation B alone. It is anticipated that Metabolic Syndrome rats administered Formulation A and B will exhibit body weights that resemble those observed in the wild-type control rats.

Effects of Administration of Formulation A and B on the blood glucose of Metabolic Syndrome rats. It is anticipated that Metabolic Syndrome rats administered Formulation A and B will have reduced blood glucose as compared to untreated Metabolic Syndrome rats. It is also anticipated that Metabolic Syndrome rats administered Formulation A and B will show a synergistic effect with respect to lower blood glucose levels as compared to Metabolic Syndrome rats treated with the individual components of Formulation A and Formulation B alone. It is anticipated that Metabolic Syndrome rats administered Formulation A and B will exhibit blood glucose levels that resemble those observed in the wild-type control rats.

Effects of Administration of Formulation A and B on HbA1c in Metabolic Syndrome rats. It is anticipated that Metabolic Syndrome rats administered Formulation A and B will have reduced HbA1c levels as compared to the untreated Metabolic Syndrome control group. It is also anticipated that Metabolic Syndrome rats administered Formulation A and B will show a synergistic effect with respect to lower levels of HbA1c as compared to Metabolic Syndrome rats treated with the individual components of Formulation A and Formulation B alone. It is anticipated that Metabolic Syndrome rats administered Formulation A and B will exhibit HbA1c levels that resemble those observed in the wild-type control rats.

These results demonstrate that the formulations of the present technology are effective in reducing elevated levels of glycated hemoglobin (HbA1c) in mammalian subjects. These results will show that administration of Formulation A and Formulation B of the present technology are useful in methods for treating Metabolic Syndrome in mammalian subjects.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth. It is understood by those of ordinary skill in the art that the labeled amounts listed in Formulations A and B represent a range that incorporates manufacturing variations in content uniformity, manufacturing overages and loss of potency over the shelf-life period that are within the prescribed regulatory limits established by regulatory bodies such as the United States Food and Drug Administration and the United States Pharmacopeia.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A thiol-containing alkyl fatty acid formulation for reducing HbA1c levels in mammalian subjects in need thereof consisting of: 600 mg alpha-lipoic acid, 400 mg L-carnitine, 100 mg CoQ10, 750 mg L-glutamine, and 1500 mg L-arginine as active ingredients, and optionally pharmaceutically acceptable carriers and excipients.

2. The thiol-containing alkyl fatty acid formulation of claim 1, wherein the alpha-lipoic acid is present as a mixture of R and S isomers.

3. The thiol-containing alkyl fatty acid formulation of claim 1, wherein the formulation is provided as an oral solid medicament in capsule form, tablet form, powder form, nanoparticle form, or nano-emulsion form for immediate or sustained release.

4. The thiol-containing alkyl fatty acid formulation of claim 1, wherein the mammalian subjects are suffering from a metabolic dysfunction, and wherein the metabolic dysfunction is metabolic syndrome, pre-diabetes, or diabetes.

* * * * *